United States Patent
Lacey

(10) Patent No.: US 11,136,540 B2
(45) Date of Patent: Oct. 5, 2021

(54) ERLENMEYER FLASK ASSEMBLIES WITH LINERS

(71) Applicant: Corning Incorporated, Corning, NY (US)

(72) Inventor: William Joseph Lacey, North Andover, MA (US)

(73) Assignee: Corning Incorporated, Corning, NY (US)

(*) Notice: Subject to any disclaimer, the term of this patent is extended or adjusted under 35 U.S.C. 154(b) by 230 days.

(21) Appl. No.: 16/095,452

(22) PCT Filed: May 19, 2017

(86) PCT No.: PCT/US2017/033450
§ 371 (c)(1),
(2) Date: Oct. 22, 2018

(87) PCT Pub. No.: WO2017/201356
PCT Pub. Date: Nov. 23, 2017

(65) Prior Publication Data
US 2019/0127674 A1    May 2, 2019

Related U.S. Application Data

(60) Provisional application No. 62/339,294, filed on May 20, 2016.

(51) Int. Cl.
*C12M 1/24* (2006.01)
*C12M 1/00* (2006.01)
(Continued)

(52) U.S. Cl.
CPC .............. *C12M 23/08* (2013.01); *B01L 3/08* (2013.01); *C12M 23/14* (2013.01); *C12M 23/24* (2013.01); *C12M 23/26* (2013.01)

(58) Field of Classification Search
None
See application file for complete search history.

(56) References Cited

U.S. PATENT DOCUMENTS 5,686,304 A    11/1997  Codner
5,789,684 A *  8/1998  Masek .................. B65D 77/06
                                          73/864.91
(Continued)

FOREIGN PATENT DOCUMENTS

AU    199539706    7/1996
CN    1145409 A    3/1997
(Continued)

OTHER PUBLICATIONS

ThomasNet, "Laboratory Glassware: Types of Laboratory Flasks", <https://www.thomasnet.com/articles/instruments-controls/types-of-lab-flasks/> Archived from the original on Apr. 22, 2015, accessed Dec. 29, 2020 (Year: 2015).*

(Continued)

*Primary Examiner* — Holly Kipouros
(74) *Attorney, Agent, or Firm* — F. Brock Riggs

(57) ABSTRACT

A flask assembly that includes: an Erlenmeyer flask; and a liner bag comprising a single opening the bag sized to fit within the flask and having a thickness from about 0.0254 mm to about 0.508 mm. The liner bag is configured for cell culturing and ease of insertion of the bag into the flask. In addition, the liner bag comprises a gas-permeable, polymeric material. Further, the liner bag can include a pocket adapted to receive a removable flask insertion element and/or at least one foldable seam configured to facilitate insertion of the bag into the flask. The liner bag can also include a vent having a gas permeability that is greater than the gas permeability of the gas-permeable, polymeric material employed in the balance of the bag.

14 Claims, 6 Drawing Sheets

(51) Int. Cl.
*C12M 1/04* (2006.01)
*B01L 3/08* (2006.01)

(56) References Cited

U.S. PATENT DOCUMENTS

| | | |
|---|---|---|
| 6,297,046 B1 | 10/2001 | Smith et al. |
| 6,673,598 B1 | 1/2004 | Akers et al. |
| 8,313,821 B2 | 11/2012 | Yan et al. |
| 2005/0015070 A1* | 1/2005 | Delnevo .................. A61J 1/18 604/408 |
| 2007/0128081 A1 | 6/2007 | Ellis et al. |
| 2008/0199357 A1 | 8/2008 | Gellman et al. |
| 2009/0298180 A1 | 12/2009 | Cattadoris et al. |
| 2011/0056951 A1* | 3/2011 | Wooldridge ......... B65D 81/267 220/495.01 |
| 2013/0101982 A1 | 4/2013 | Jones et al. |
| 2014/0287512 A1 | 9/2014 | Kaisermayer et al. |
| 2017/0158996 A1* | 6/2017 | Kimura .................. C12M 23/14 |

FOREIGN PATENT DOCUMENTS

| | | |
|---|---|---|
| CN | 204323928 U | 5/2015 |
| CN | 204356343 U | 5/2015 |
| CN | 204474691 U | 7/2015 |
| JP | 2008-539145 | 11/2008 |
| WO | 2006/116389 A2 | 11/2006 |
| WO | 2007/143579 A2 | 12/2007 |
| WO | 2016/027800 A1 | 2/2016 |

OTHER PUBLICATIONS

Goldman's Cecil Medicine, Ed. Goldman et al., 24th edition, 2012, p. 818 (Year: 2012).*
Bito et al., Patterns of cellular organization and cell division in the epithelium of the cultured lens, Exp. Eye Res., 1965, vol. 4, pp. 146-161 (Year: 1965).*
Falch et al., Disposable shaker flasks, Biotechnology and Bioengineering, 1963, vol. V, pp. 211-220 (Year: 1963).*
Mirabello, Influence of siderophore producing bacteria will affect cadmium uptake by *Brassica napsus* in the presence of goethite, thesis, Cornell University, 2006 (Year: 2006).*
International Search Report and Written Opinion of the International Searching Authority; PCT/US2017/033450; dated Aug. 21, 2017; 10 Pages; European Patent Office.
Chinese Patent Application No. 201780031276.8, Office Action dated Mar. 15, 2021, 10 pages (English Translation Only); Chinese Patent Office.
Japanese Patent Application No. 2018-560199, Office Action dated Jan. 27, 2021, 6 pages (3 pages of English Translation and 3 pages of Original Document); Japanese Patent Office.
Japanese Patent Application No. 2018-560199, Decision To Grant dated Jul. 28, 2021, 5 pages (2 pages of English Translation and 3 pages of Original Document), Japan Patent Office.

* cited by examiner

ERLENMEYER FLASK ASSEMBLIES WITH LINERS

CROSS-REFERENCE TO RELATED APPLICATIONS

This is a national stage application under 35 U.S.C. § 371 of International Application No. PCT/US2017/033450, filed on May 19, 2017, which claims the benefit of U.S. Provisional Application Serial No. 62/339,294 filed on May 20, 2016, the content of which is relied upon and incorporated herein by reference in its entirety.

BACKGROUND

The present disclosure relates generally to flask apparatus for cell culturing and, more particularly, liners for Erlenmeyer flasks and Erlenmeyer flask assemblies with liners for cell culturing.

Cost and contamination are concerns when using Erlenmeyer flasks for cell culturing. Erlenmeyer flasks are often used only for a single run in view of contamination concerns, leading to high costs for cell culturing operations. Further, efforts to clean and autoclave Erlenmeyer flasks for re-use often leave these flasks subject to contamination risks for future cell culture runs, despite exceedingly high care in the cleaning and autoclaving steps. As the contamination risks are minimized through additional or enhanced cleaning and autoclaving steps, the overall cell culturing costs can significantly increase as a function of these contamination removal processes.

Cell culturing in Erlenmeyer flasks can also be performance-limited. While single-use Erlenmeyer flasks can be successfully employed to develop cell cultures, the efficiency of these processes can be limited by the gas exchange in proximity to the cell cultures afforded by the flask configuration and geometry. Many efforts to improve gas exchange, including direct gas introduction schemes, can add further cost to the overall cell culturing operation.

Accordingly, there is a need for Erlenmeyer flask technologies that offer reduced cell culturing costs and less contamination risk. There is also a need for Erlenmeyer flask technologies that can offer improved cell culturing performance.

SUMMARY

An aspect of the disclosure pertains to a liner for an Erlenmeyer flask that includes a liner bag comprising a single opening, the bag sized to fit within the flask and having a thickness from about 0.0254 mm to about 0.508 mm. Further, the liner bag is configured for cell culturing and ease of insertion into the flask. In addition, the liner bag comprises a gas-permeable, polymeric material.

In some embodiments of the liner, the liner bag further includes a pocket adapted to receive a removable flask insertion element. The liner bag, in certain aspects, can also include a vent, the vent having a gas permeability that is greater than the gas permeability of the gas-permeable, polymeric material of the liner bag. The vent can also include a membrane with an average pore size from about 0.2 microns to about 5 microns. In other implementations of the liner, the liner bag can also include at least one foldable seam configured to facilitate insertion of the bag into the flask.

In a further aspect of the disclosure, a flask assembly is provided that includes: an Erlenmeyer flask; and a liner bag comprising a single opening, the bag sized to fit within the flask and having a thickness from about 0.0254 mm to about 0.508 mm. Further, the liner bag is configured for cell culturing and ease of insertion into the flask. In addition, the liner bag comprises a gas-permeable, polymeric material.

In some embodiments of the foregoing flask assembly, the liner bag further includes a pocket adapted to receive a removable flask insertion element. In other aspects of the flask assembly, the liner bag has a thickness of about 0.0254 mm to about 0.254 mm. In a further embodiment of the foregoing flask assembly, the liner bag further includes at least one foldable seam configured to facilitate insertion of the bag into the flask.

In other embodiments of the foregoing flask assembly, the liner bag in the flask assembly can also include a vent, the vent having a gas permeability that is greater than the gas permeability of the gas-permeable, polymeric material of the liner bag. The vent can also include a membrane with an average pore size from about 0.2 microns to about 5 microns. In another embodiment of the foregoing flask assembly, the flask can include a cutout that is sized and positioned to correspond to the vent of the liner bag, as inserted within the flask.

In another aspect of the disclosure, a flask assembly is provided that includes: an Erlenmeyer flask comprising a plurality of flask portions; and a liner bag comprising a single opening and sized to fit within the flask. Further, each of the flask portions is configured to couple with at least one of the other flask portions. In addition, the liner bag is configured for cell culturing and comprises a gas-permeable, polymeric material.

In an embodiment of the foregoing flask assembly with an Erlenmeyer flask comprising a plurality of flask portions, the liner bag can have a thickness from about 0.254 mm to about 0.508 mm. Further, the liner bag can include a vent, the vent having a gas permeability that is greater than the gas permeability of the gas-permeable, polymeric material of the liner bag. The vent can also include a membrane with an average pore size from about 0.2 microns to about 5 microns. In an another embodiment of the foregoing flask assembly, the flask can include a cutout that is sized and positioned to correspond to the vent of the liner bag, as inserted within the flask.

In another embodiment of the foregoing flask assembly, each of the flask portions further include a registration feature configured to aid in mechanically coupling with the registration feature of at least one of the other flask portions.

According to additional aspects of the liner bags and flask assemblies of the disclosure, the liner bag can comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof. Further, in embodiments of the liner bag having a vent that includes a membrane, the membrane can comprise a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof. In further embodiments, the liner bag can include a base and sides, and further wherein the sides comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

Additional features and advantages will be set forth in the detailed description which follows, and will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the disclosure as it is claimed.

The accompanying drawings are included to provide a further understanding of principles of the disclosure, and are incorporated in, and constitute a part of, this specification. The drawings illustrate one or more embodiment(s) and, together with the description, serve to explain, by way of example, principles and operation of the disclosure. It is to be understood that various features of the disclosure disclosed in this specification and in the drawings can be used in any and all combinations. By way of non-limiting examples, the various features of the disclosure may be combined with one another according to the following aspects.

DETAILED DESCRIPTION

Figure 1:
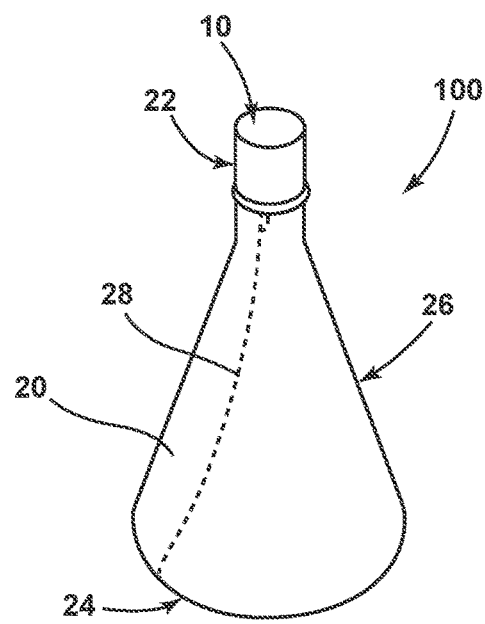
FIG. 1 is a schematic, perspective view of a liner with a foldable seam for an Erlenmeyer flask according to an aspect of the disclosure.

In the following detailed description, for purposes of explanation and not limitation, example embodiments disclosing specific details are set forth to provide a thorough understanding of various principles of the present disclosure. However, it will be apparent to one having ordinary skill in the art, having had the benefit of the present disclosure, that the present disclosure may be practiced in other embodiments that depart from the specific details disclosed herein. Moreover, descriptions of well-known devices, methods and materials may be omitted so as not to obscure the description of various principles of the present disclosure. Finally, wherever applicable, like reference numerals refer to like elements.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

As used herein, the singular forms "a," "an" and "the" include plural referents unless the context clearly dictates otherwise. Thus, for example, reference to a "component" includes aspects having two or more such components, unless the context clearly indicates otherwise.

Aspects of the disclosure generally pertain to Erlenmeyer flask technologies and assemblies that offer reduced cell culturing costs, less contamination risk, and enhanced cell culturing performance. These flask technologies and assemblies include liners comprising liner bags for Erlenmeyer flasks for cell culturing in which the liner bags are configured for single-use and the flasks are retained for multi-use. These flask technologies also comprise flask assemblies that include an Erlenmeyer flask, and a liner bag sized for the flask. Further, the bag is configured for cell culturing, ease of insertion into the flask and for single use. In addition, the flask technologies also comprise flask assemblies that include an Erlenmeyer flask with a plurality of flask portions, and a liner bag sized for the flask. Further, the bag is configured for cell culturing and single use.

The flask technologies of the disclosure offer several advantages. First, these flask technologies offer significant cost savings over conventional approaches. In particular, the disposal and replacement costs associated with the single use liners and liner bags are significantly lower than the disposal costs associated with those of single use flasks. Further, the overall cost of cell culturing operations should be reduced with the flask technologies of the disclosure, none of which require autoclaving or other cleaning between uses for most cell culturing applications. Also, liners as disclosed herein may be pre-sterilized, and thus provide a sterile environment in which to initiate and maintain cell cultures. The sterile environment provided by flask technologies of the present disclosure effectively reduces or eliminates contamination concerns associated with conventional flask technologies. In addition, several of the flask technologies of the disclosure include vents, membranes and other more permeable features that are configured to enhance gas exchange with the cultured cells within the flasks, thus eliminating the need for additional, costly gas exchange measures (e.g., tubes and the like inserted into the flasks for direct gas supply and exchange with the cell cultures). The liners disclosed herein Referring to FIG. 1, a liner 100 for an Erlenmeyer flask is depicted according to an aspect of the disclosure. As shown, the liner 100 includes a liner bag 20 comprising a single opening 10, the bag sized to fit within the flask and configured for cell culturing. Further, the liner bag 20 includes a neck 22, base 24 and sides 26.

Further, the liner bag 20 of the liner 100 depicted in FIG. 1 can be configured with a thickness from about 0.0254 mm to about 0.508 mm, 0.254 mm to 0.508 mm and 0.0254 mm to 0.254 mm. For example, the thickness of the liner bag can be 0.0254 mm, 0.03 mm, 0.04 mm, 0.05 mm, 0.06 mm. 0.07 mm, 0.08 mm, 0.09 mm, 0.10 mm, 0.2 mm, 0.3 mm, 0.4 mm, 0.5 mm, 0.508 mm, and all thicknesses between these values. More generally, smaller thicknesses of the liner bag 20 (e.g., thicknesses that range from 0.0254 mm to 0.254 mm) within these ranges can enhance insertion of the liner bag 20 into an Erlenmeyer flask by facilitating folding and/or rolling of the bag prior to insertion of the bag through the opening of the flask. Smaller thicknesses can, in some embodiments, improve the gas exchange and supply to cell cultures and media within the liner bag 20 by reducing the permeability of the bag. In other aspects, larger thicknesses of the liner bag 20 (e.g., thicknesses that range from 0.254 mm to 0.508 mm) can also enhance insertion of the liner bag into an Erlenmeyer flask by facilitating the development of a rigid roll that can be inserted into the flask. Still further, larger thicknesses of the liner bag 20 (e.g., thicknesses that range from 0.254 mm to 0.508 mm) can also afford the bag with better shape control within the flask to maximize the space available in the bag 20 for cell culturing, particularly for embodiments of the disclosure employing multi-piece flasks that do not require insertion of the bag through the opening of the flask (see, e.g., FIGS. 6, 6A).

The liner bag 20 of the liner 100 depicted in FIG. 1 can also be configured with foldable seams and related features for ease of insertion into an Erlenmeyer flask. For example, in certain embodiments, the liner 100 employs a liner bag 20 with at least one foldable seam 28 to facilitate insertion of the bag 20 into an Erlenmeyer flask. As shown in FIG. 1, a foldable seam 28 runs along a side 26 of the liner bag 20 to facilitate folding or rolling of the liner bag 20 into a tube-like arrangement (see FIG. 1A) that is better-suited for insertion into an opening of an Erlenmeyer flask. According to other embodiments, foldable seams 28 can be integrated into the base 24 of the liner bag 20. The foldable seams 28 can be integral with the liner bag 20 or comprise separate material, e.g., stitched into the bag 20. Those with ordinary skill in the field can readily appreciate that other geometries of the one or more seams 28 can be incorporated into the bag 20 to facilitate its insertion into an Erlenmeyer flask.

Figure 2:
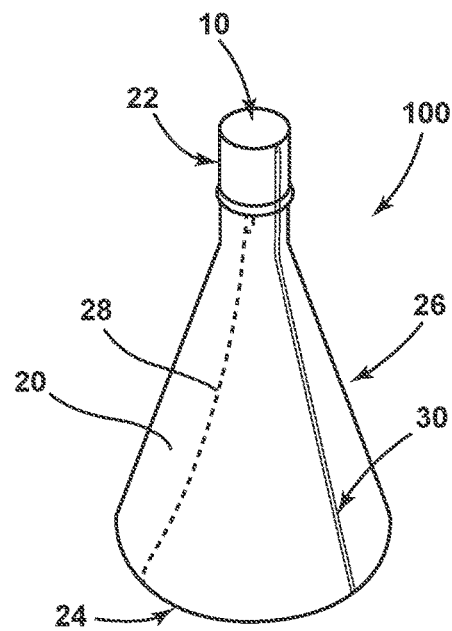
FIG. 2 is a schematic, perspective view of a liner with a foldable seam and a flask insertion pocket for an Erlenmeyer flask, according to an aspect of the disclosure.

As shown in FIG. 2, the liner bag 20 of the liner 100 can also be configured with a pocket 30 adapted to receive a removable flask insertion element, e.g., a wire 40 (see FIG. 2A), to facilitate the insertion of the bag into an Erlenmeyer flask. As shown in FIG. 2, the pocket 30 runs along a side 26 of the liner bag 20 and is configured to accept a removable, flask insertion element, such as a wire 40 or other similarly-shaped element. Upon insertion of the wire 40, or a similarly-configured element, into the pocket 30, the user can direct the liner bag 20 into the opening of the Erlenmeyer flask (see, e.g., FIG. 2B) and then remove the wire 40 upon placement of the bag 20 within the flask (see, e.g., FIG. 2C). According to other embodiments, the pocket 30 can be integral with the liner bag 20 or comprise a separate material, e.g., as stitched into a pocket-like form along a side 26 of the liner bag 20.

As shown in FIGS. 1 and 2 in exemplary form, the liner bag 20 of the liner 100 comprises a gas-permeable, polymeric material. This ensures that media and cell cultures (e.g., cultures 300 shown in FIG. 7) that are grown within the bag 20 have a sufficient supply of gas and gas exchange for proper growth. Accordingly, the material employed for the liner bag 20 should exhibit gas permeability levels that are sufficient for the intended cell culturing application and with a sufficient thickness to support ease of insertion into an Erlenmeyer flask. In certain implementations, the liner bag 20 can be fabricated from various polymeric materials including low density polyethylene (LDPE), polyethylene (PE), ethyl vinyl acetate (EVA), silicone, fluorinated ethylene propylene (FEP), polytetrafluoroethylene (PTFE) (e.g., Chemours™ Company Teflon® PTFE material), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof.

Figure 3:
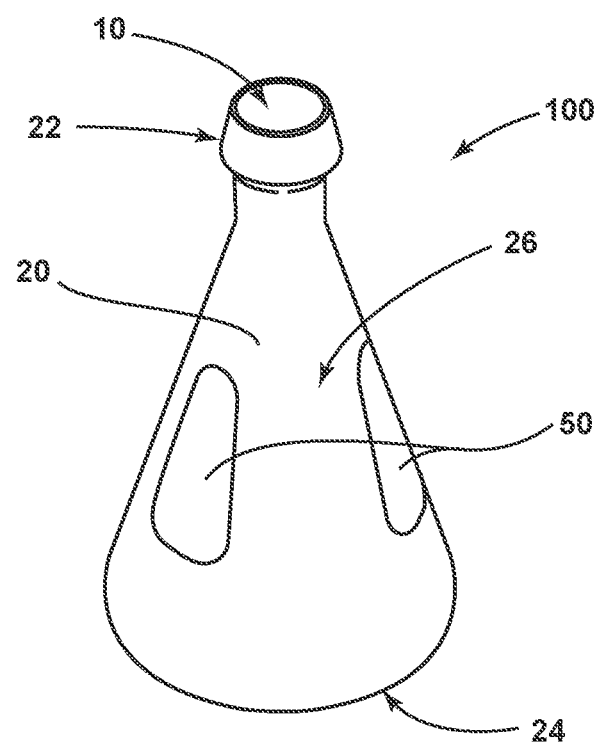
FIG. 3 is a schematic, perspective view of a liner with a plurality of vents for an Erlenmeyer flask, according to an aspect of the disclosure.

According to another aspect of the liner 100, the liner bag 20, as shown in FIG. 3, can include one or more vents 50. The vents 50 can be configured with higher gas permeability levels in comparison to the gas permeability level of the balance of the polymeric, gas-permeable material employed in the remainder of the bag 20. As such, the bag 20 can be configured with highly-permeable vents 50 for enhanced gas exchange and cell culturing capabilities but retain sufficient rigidity through the choice of less-permeable materials for the balance of the bag 20 (e.g., in the sides 26 and base 24) to facilitate ease of insertion into an Erlenmeyer flask.

According to one implementation of a liner 100 with a liner bag 20 that incorporates one or more vents 50 (see FIG. 3), each vent 50 is fabricated from a membrane with an average pore size from about 0.2 microns to about 5 microns. For example, the average pore size of the vents can be 0.2 microns, 0.3 microns, 0.4 microns, 0.5 microns, 0.6 microns, 0.7 microns, 0.8 microns, 0.9 microns, 1 micron, 1.5 microns, 2 microns, 2.5 microns, 3 microns, 3.5 microns, 4 microns, 4.5 microns, 5 microns and all average pore sizes between these pore size values. In certain aspects, the membrane employed for the vents 50 is hydrophobic to minimize adhesion of the cell cultures and other liquid media to the vents 50. In an additional embodiment of the liner 100, the liner bag 20 incorporates vents 50 that are fabricated in a membrane form from various polymeric materials including polytetrafluoroethylene (PTFE) (e.g., Chemours™ Company Teflon® PTFE material), perfluoroalkoxy alkane (PFA), high density polyethylene (HDPE) fabric (e.g., E. I. du Pont de Nemours and Company Tyvek® material), polyvinylidene fluoride (PVDF) and acrylic copolymer (e.g., Pall Corporation Versapor® membrane materials), nylon and combinations thereof.

According to another implementation of a liner 100 with a liner bag 20 that incorporates vents 50 (see FIG. 3), the sides 26 of the bag can be fabricated from various polymeric materials including low density polyethylene (LDPE), polyethylene (PE), ethyl vinyl acetate (EVA), silicone, fluorinated ethylene propylene (FEP), polytetrafluoroethylene (PTFE) (e.g., Chemours™ Company Teflon® PTFE material), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof; and the base 24 of the bag can be fabricated from polytetrafluoroethylene (PTFE) materials, platinum-cured silicone materials and other non-stick materials to minimize adhesion of cells to the base during cell culturing, thus enhancing cell culturing yields. In these configurations, the vent or vents 50 and the base 24 of the liner bag 20 can enhance the gas exchange to the cell cultures within the bag by virtue of their higher gas permeability levels in comparison to the material or materials used to fabricate the sides 26 of the bag. While these multi-material configurations for the liner 100 with one or more vents 50 present higher material and product costs than other aspects of the liners 100 in the disclosure fabricated from one material without vents, certain applications for the liner 100 can benefit from the enhanced cell culturing capability offered by these configurations.

Figure 1A:
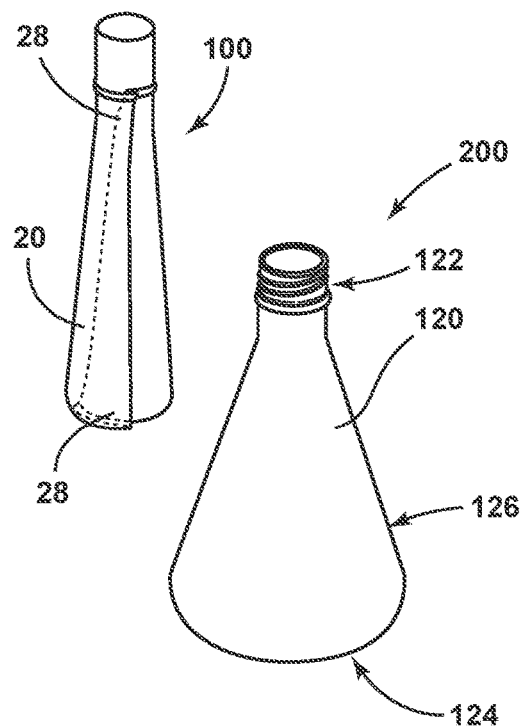
FIG. 1A is a schematic, perspective view of a flask assembly with the liner depicted in FIG. 1, as folded for insertion into the flask assembly, according to an aspect of the disclosure.

Referring now to FIG. 1A, a flask assembly 200 is depicted with a liner 100 (see, e.g., FIG. 1) according to another aspect of the disclosure. As shown in FIG. 1A, the liner 100 incorporated into the flask assembly 200 can be configured with the same features and variants as outlined earlier (see, e.g., the liner 100 with a foldable seam 28 depicted in FIG. 1, the liner 100 with a foldable seam 28 and pocket 30 depicted in FIG. 2, and the liner 100 with vents 50 depicted in FIG. 3). As such, like-numbered elements have the same or similar structure and functions, unless otherwise noted. With further regard to the flask assembly 200 shown in FIG. 1A, the assembly includes: an Erlenmeyer flask 120; and a liner bag 100 comprising a single opening 10 (see FIG. 1), the bag sized to fit within the flask 120 and having a thickness from about 0.0254 mm to about 0.508 mm. As shown in exemplary form in FIG. 1A, the flask 120 includes a neck 122, base 124 and sides 126. Further, the liner bag 20 of the assembly 200, as fabricated from a gas-permeable, polymeric material, is configured for cell culturing and ease of insertion into the flask 120.

The flask 120 depicted in FIG. 1A can be fabricated from a glass (e.g., Corning® Inc. Pyrex®), glass-ceramic, ceramic, polymer, metal, composite or combinations thereof. In preferred embodiments, the flask 120 is fabricated from a material typically understood by those with ordinary skill in the field for Erlenmeyer flasks with suitable strength, fracture toughness, temperature resistance and leach resistance for cell culturing. Further, the flask 120 can be fabricated by any number of acceptable manufacturing methods understood by those with skill in the field of the disclosure. In certain implementations, the flask 120 can be fabricated from a polycarbonate material and its thickness can be limited to no greater than 2 mm to maintain optical clarity and ensure that the flask 120 is reusable after an autoclaving process.

Figure 1B:
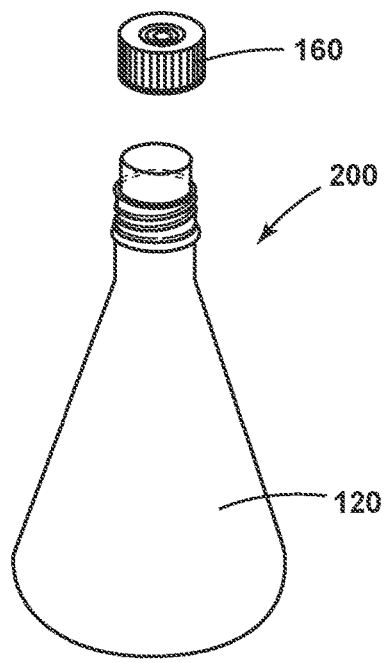
FIG. 1B is a schematic, perspective view of the flask assembly depicted in FIG. 1A, as assembled prior to enclosure with a vent cap.

Referring again to FIG. 1A, aspects of the flask assembly 200 incorporate a liner 100 with a liner bag 20 configured for ease of insertion through the opening in the neck 122 of the flask 120. More particularly, the liner bag 20 can be rolled or otherwise folded into a form to facilitate its insertion into the flask 120. In certain aspects, as shown in FIG. 1A, the liner bag 20 can be folded along one or more of its seams 28 for this purpose. Upon insertion of the liner bag 20 into the flask 120, the liner bag 20 can expand to fill the interior volume of the flask 120 for efficient cell culturing as shown in FIG. 1B. Depending on the thickness of the liner bag 20, it can be folded over the neck 122 (see FIG. 1A), cut or otherwise sized to ensure that a vent cap 160 (see FIG. 1B) can be secured over the neck 122 of the flask 120.

Figure 2A:
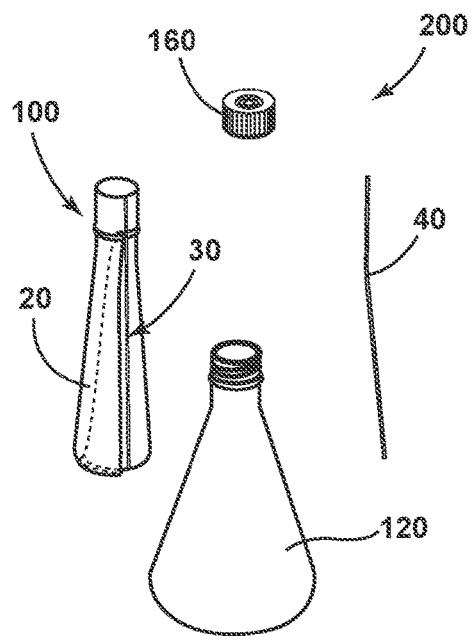
FIG. 2A is a schematic, perspective view of a flask assembly with the liner depicted in FIG. 2, as folded for insertion into the flask assembly, according to an aspect of the disclosure.
Figure 2B:
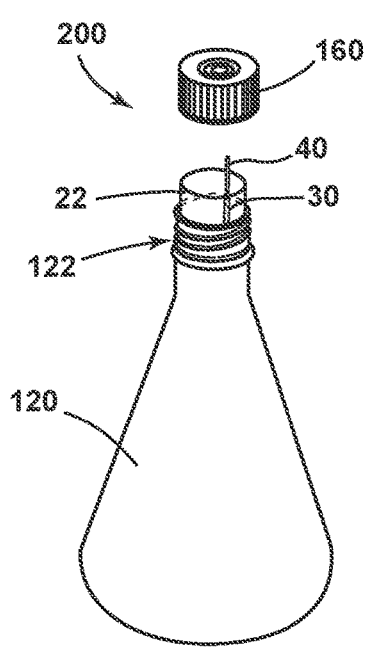
FIG. 2B is a schematic, perspective view of the flask assembly depicted in FIG. 2A, as assembled with a wire flask insertion element prior to enclosure with a vent cap.
Figure 2C:
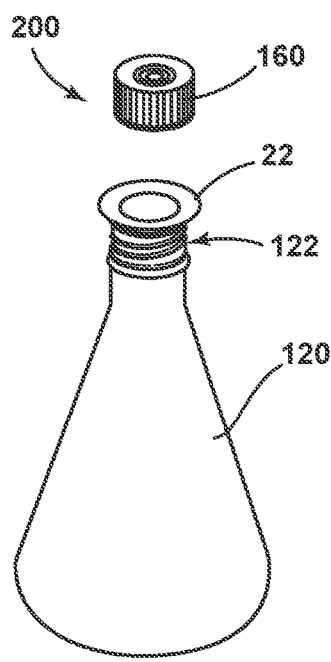
FIG. 2C is a schematic, perspective view of the flask assembly depicted in FIG. 2A, as assembled with the liner bag partially folded over the neck of the flask, prior to enclosure with a vent cap.
Figure 2D:
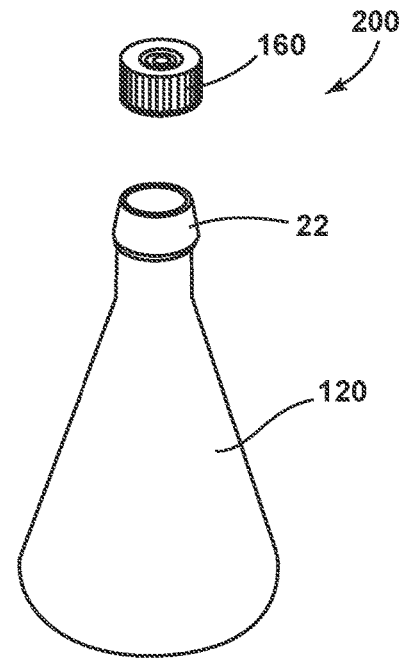
FIG. 2D is a schematic, perspective view of the flask assembly depicted in FIG. 2A, as assembled with the liner bag fully folded over the neck of the flask, prior to enclosure with a vent cap.

Referring now to FIGS. 2-2D, a flask assembly 200 is depicted with a liner 100 according to an additional aspect of the disclosure. As shown in FIG. 2, the liner 100 includes a liner bag 20 that is configured with at least one foldable seam 28 and a pocket 30. The liner 100 can be rolled along one or more of the seams 28, leaving the pocket 30 accessible for a wire 40, as shown in FIG. 2A. Both of these features can be employed to facilitate insertion of the liner bag 20 into the flask 120. As shown in FIG. 2B, the liner bag 20 is inserted into the flask 120 (i.e., with its neck 22 just outside the neck 122 of the flask 120) and a wire 40 has been introduced into the pocket 30 to facilitate the insertion. As also shown in FIG. 2B, the neck 22 of the liner bag 20 (see FIG. 2A) is exposed above the neck 122 of the flask 120. The neck 22 of the liner bag 20 can then be folded over the neck 122 of the flask 120 to provide clearance for the installation of a vent cap 160 to close the opening of the flask 120, as shown in FIGS. 2C and 2D. After cell cultures are introduced into the liner bag 20 of the assembly 200, the vent cap 160 can be fastened onto the flask 120 and cell culturing can be initiated in the assembly 200.

According to a further aspect of the disclosure, the flask assembly 200 can employ a liner 100, as depicted in FIG. 3, for an Erlenmeyer flask, such as flask 120 (see, e.g., flasks 120 in FIGS. 1B, 2B), the liner 100 having a liner bag 20 with a plurality of vents 50. As noted earlier, the liner bag 20 can include one or more vents 50. The vents 50 can be configured with higher gas permeability levels in comparison to the gas permeability level of the balance of the polymeric, gas-permeable material employed in the remainder of the bag 20. As such, the bag 20 can be configured with highly-permeable vents 50 for enhanced gas exchange and cell culturing capabilities but retain sufficient rigidity through the choice of less-permeable materials for the balance of the bag 20 (e.g., in the sides 26 and base 24) to facilitate ease of insertion into an Erlenmeyer flask. Further, in certain implementations, the vents 50 of the liner bag 20 are fabricated with a hydrophobic membrane or hydrophobic membrane-containing material to minimize adhesion of cell cultures and liquid media to the vents 50, which would otherwise inhibit gas exchange. The flask assembly 200 can also employ a liner 100 with a liner bag 20 in which each vent 50 (FIG. 3) is fabricated from a membrane with an average pore size from about 0.2 microns to about 5 microns. In an additional embodiment, the liner bag 20 incorporates vents 50 that are fabricated in a membrane form from various polymeric materials including polytetrafluoroethylene (PTFE) (e.g., Chemours™ Company Teflon® PTFE material), perfluoroalkoxy alkane (PFA), high density polyethylene (HDPE) fabric (e.g., E. I. du Pont de Nemours and Company Tyvek® material), polyvinylidene fluoride (PVDF) and acrylic copolymer (e.g., Pall Corporation Versapor® membrane materials), nylon and combinations thereof. Still further, the sides 26 of the bag 20 can be fabricated from various polymeric materials including low density polyethylene (LDPE), polyethylene (PE), ethyl vinyl acetate (EVA), silicone, fluorinated ethylene propylene (FEP), polytetrafluoroethylene (PTFE) (e.g., Chemours™ Company Teflon® PTFE material), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base 24 of the bag can be fabricated from polytetrafluoroethylene (PTFE) and a platinum-cured silicone materials.

Figure 4:
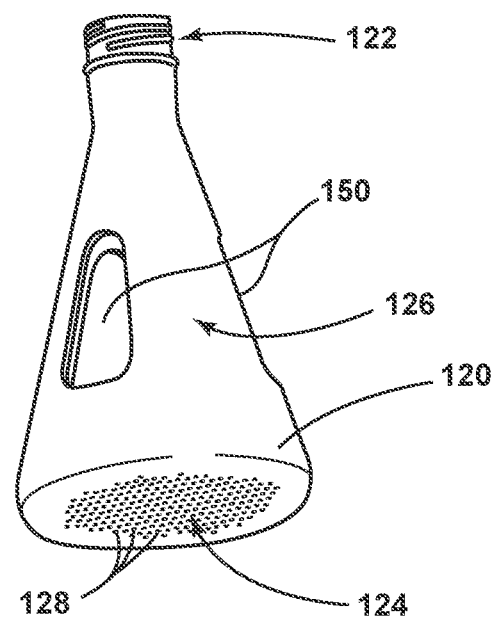
FIG. 4 is a schematic, perspective view of a flask with cutouts that are sized and positioned to correspond to the vents of the liner depicted in FIG. 3, according to an aspect of the disclosure.

According to another aspect, the flask assembly 200 can employ a liner 100 having a liner bag 20 with an opening 10, the bag sized to fit within an Erlenmeyer flask, such as flask 120 with a plurality of cutouts 150, as depicted in FIG. 4. These cutouts 150 in the flask 120 shown in FIG. 4 can be sized and positioned to correspond to the vents 50 of the liner 100 (see FIG. 3). In other aspects of the flask assembly 200, the cutouts 150 are incorporated into the flask 120 and the liner bag 20 is configured without vents 50. In these configurations of the assembly 200, the cutouts 150 can aid in gas exchange with cell cultures within a liner bag 20, independent of the inclusion of vents 50 within the liner bag 20. In an additional aspect of the flask assembly 200, the flask 120 can be configured with perforations 128 in its base 124 to further enhance gas exchange with cell cultures located within the liner bag 20, and augment the gas exchange afforded by the cutouts 150 in the flask 120 and/or the vents 50 incorporated into the liner bag 20.

Figure 5:
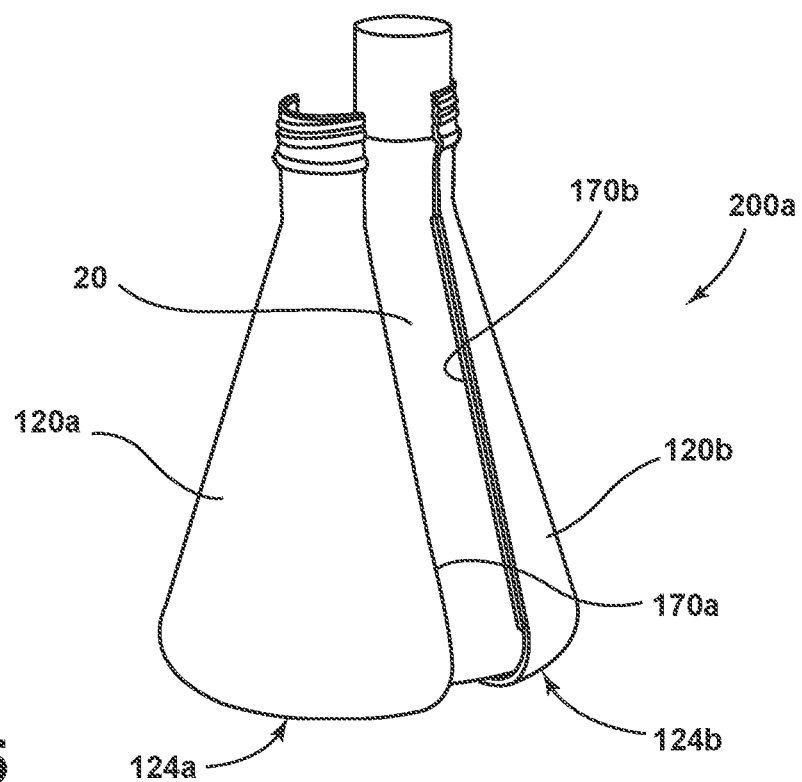
FIG. 5 is a schematic, perspective view of a flask assembly that includes a flask having two flask portions with registration features, and a liner according to an aspect of the disclosure.
Figure 5A:
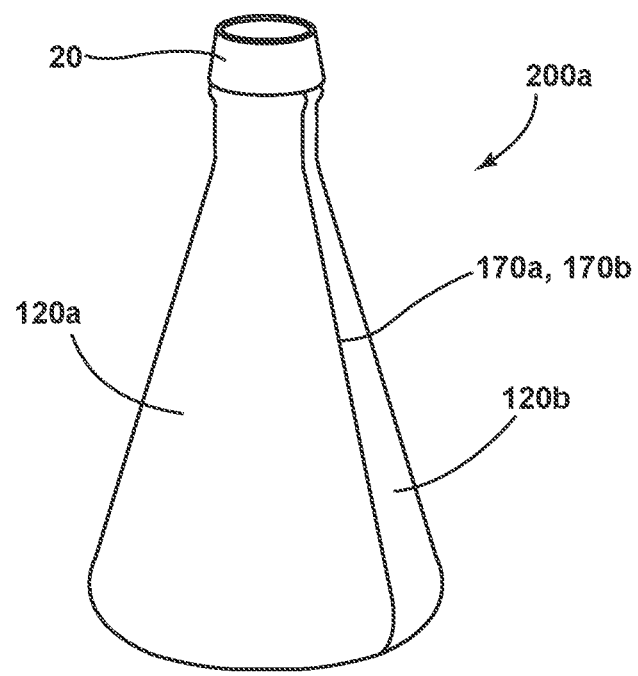
FIG. 5A is a schematic, perspective view of the flask assembly depicted in FIG. 5, as assembled.

According to an additional aspect of the disclosure, a flask assembly 200a is depicted in FIGS. 5 and 5A that includes a flask with a plurality of flask portions, e.g., two flask portions 120a, 120b with optional registration features 170a, 170b. As recognized by those with ordinary skill in the field, flask assembly 200a can incorporate a flask including more than two portions, which may offer manufacturing and/or packaging benefits. Further, the assembly 200a includes a liner bag 20 having a single opening and sized to fit within the flask 120a (e.g., the liner bags 20 shown in FIGS. 1, 2, and 5). The liner bag 20 of the flask assembly 200a is configured for cell culturing and comprises a gas-permeable material. The flask portions 120a, 120b, can include bases 124a, 124b and are generally fabricated from a glass material (e.g., Corning® Inc. Pyrex®). Further, the flask portions 120a, 120b can be fabricated from a glass (e.g., Corning® Inc. Pyrex®), glass-ceramic, ceramic, polymer, metal, composite or combinations thereof. In preferred embodiments, the flask portions 120a, 120b are fabricated from a material typically understood by those with ordinary skill in the field for Erlenmeyer flasks with suitable strength, fracture toughness, temperature resistance and leach resistance for cell culturing. Further, the flask portions 120a, 120b can be fabricated by any number of acceptable manufacturing methods understood by those with skill in the field of the disclosure. In certain implementations, the flask portions 120a, 120b can be fabricated from a polystyrene material and their thicknesses can be limited to no greater than 2 mm to maintain optical clarity. Advantageously, in this configuration of the flask assembly 200a, the liner bag 20 can be directly placed within one of the flask portions 120a or 120b, without resorting to an additional step of folding the bag 20, providing guidance to the bag 20 by a wire (e.g., wire 40 as shown in FIG. 2A) and/or relying on some other external feature to place the bag 20 within the flask.

In another aspect of the flask assembly 200a depicted in FIGS. 5 and 5A, the flask can include flask portions 120a, 120b, each configured to couple with at least one of the other flask portions. In certain implementations, the registration features 170a, 170b can be incorporated into the flask portions 120a, 120b. Accordingly, some implementations will employ portions 120a, 120b fabricated from polymers or metals to facilitate coupling, joining and/or locking of these elements together, particularly with registration features 170a, 170b. After placement of the liner bag 20, which is fabricated from a gas-permeable, polymeric material, within one of the flask portions 120a, 120b, the flask portion in which the liner bag 20 is not positioned within can be aligned with, and mechanically coupled to, one of the other flask portions by virtue of the registration features 170a, 170b. In some embodiments, the registration features 170a, 170b can include locking ribs, magnets, snap-fit interfaces and other mechanical or electro-mechanical (e.g., magnets) features to facilitate mechanical coupling of the flask portions 120a, 120b after the liner bag 20 has been introduced into the flask.

Figure 6:
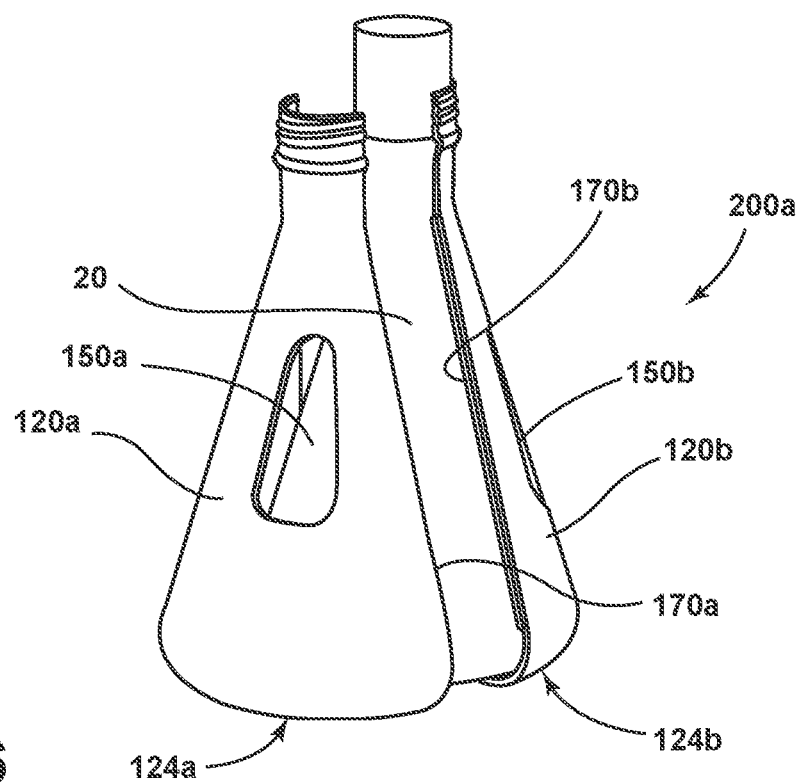
FIG. 6 is a schematic, perspective view of a flask assembly that includes a flask having two flask portions comprising vents and registration features, and a liner according to an aspect of the disclosure.
Figure 6A:
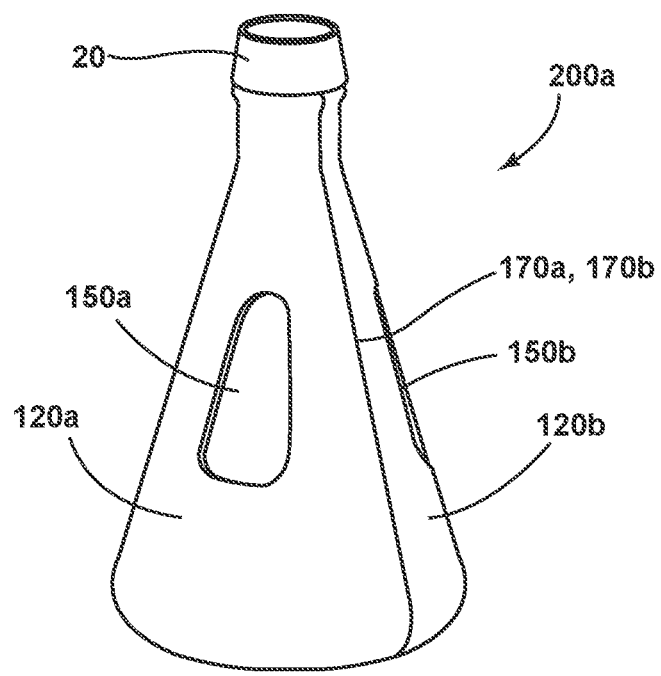
FIG. 6A is a schematic, perspective view of the flask assembly depicted in FIG. 6, as assembled.

Referring now to FIGS. 6 and 6A, a flask assembly 200a according to another embodiment is depicted that is configured similarly to the flask assembly 200a depicted in FIGS. 5 and 5A. Accordingly, like-numbered elements have the same or similar structures and functions. The flask assembly 200a depicted in FIGS. 6 and 6A, however, includes a flask having two flask portions 120a, 120b with registration features 170a, 170b; and cutouts 150a, 150b. These cutouts 150a, 150b can be sized and positioned to correspond to the vents 50 of a liner bag 20 of a liner 100 (see FIG. 3). In other aspects of the flask assembly 200a, the cutouts 150a, 150b are incorporated into the flask portions 120a, 120b and the liner bag 20 is configured without any vents. In these configurations of the assembly 200a, the cutouts 150a, 150b can aid in gas exchange with cell cultures within a liner bag 20, independent of the inclusion of vents 50 within the liner bag 20. In an additional aspect of the flask assembly 200a, the flask portions 120a, 120b can be configured with perforations (see perforations 128 depicted in FIG. 4) in their respective base portions 124a, 124b. These perforations in the base portions 124a, 124b in the flask portions 120a, 120b can further enhance gas exchange with cell cultures located within the liner bag 20, and augment the gas exchange afforded by the cutouts 150a, 150b in the flask and/or the vents 50 incorporated into the liner bag 20.

Figure 7:
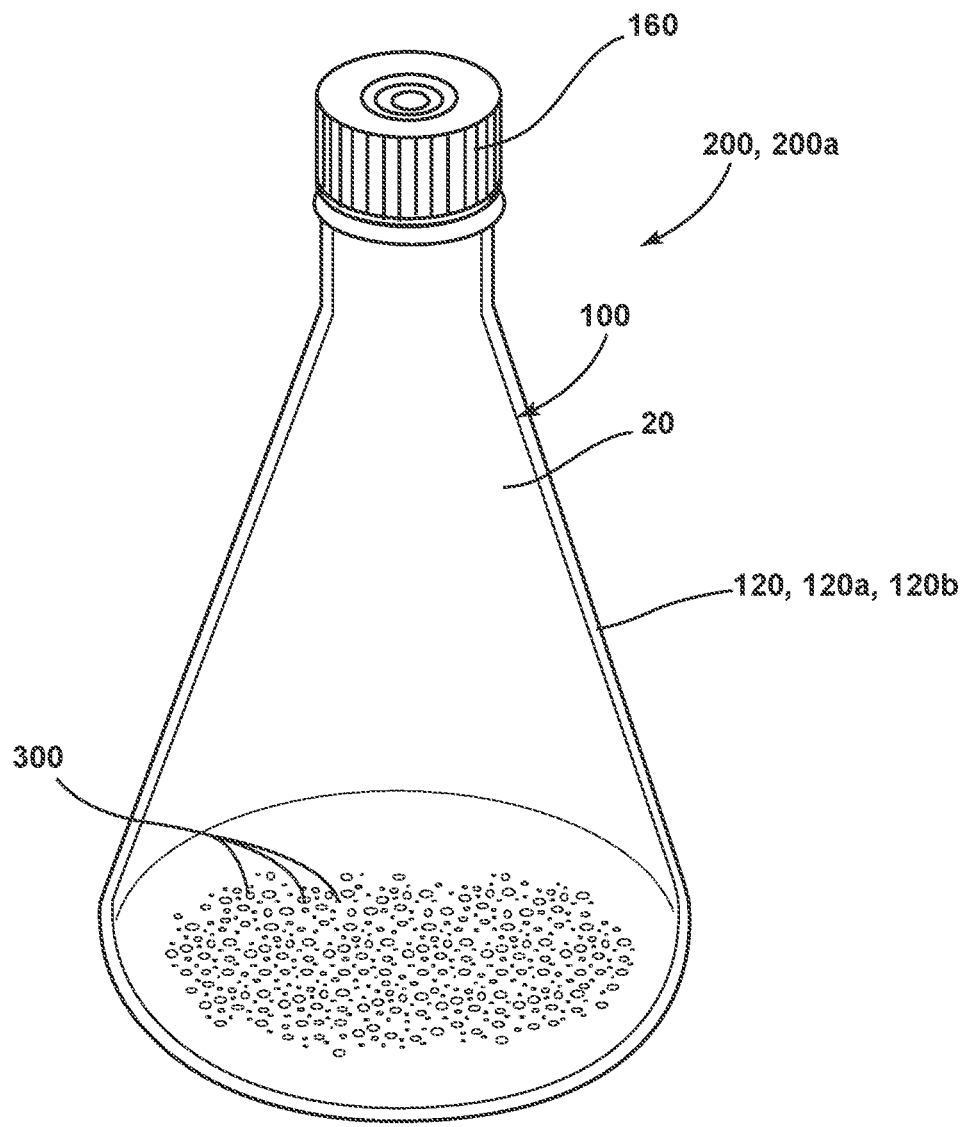
FIG. 7 is a schematic, cut-away view of flask assemblies according to aspects of the disclosure.

Referring now to FIG. 7, flask assemblies 200, 200a and a corresponding liner 100 are depicted as-assembled, in a cut-away exemplary view. More particularly, the flask assemblies 200, 200a are shown with a respective flask 120 or flask portions 120a, 120b, along with a vent cap 160 enclosing the liner 100, which comprises a liner bag 20.

Further, the flask assemblies 200, 200a and liners 100 are schematically depicted in FIG. 7 with cell cultures 300 contained with the liner bag 20. More generally, the flask assemblies 200, 200a, liners 100, and other assemblies and liners consistent with the construction and design principles of these aspects of the disclosure, offer significant cost savings over approaches that employ conventional Erlenmeyer flasks for cell culturing. In particular, the disposal and replacement costs associated with the single use liners (e.g., liner 100) and liner bags (e.g., liner bag 20) of flask assemblies 200, 200a (and other flask assemblies compatible with liners 100) are significantly lower than the disposal costs associated with those of single use flasks. Further, the overall cost of cell culturing operations is expected to be reduced with these flask technologies, none of which require autoclaving or other cleaning between uses for most cell culturing applications. In addition, several embodiments of the flask assemblies 200, 200a and liners 100 (see, e.g., liners 100 depicted in FIGS. 1, 2 and 3) of the disclosure include vents (e.g., vents 50), membranes and other more permeable features (e.g., perforations 128 depicted in FIG. 4) that are configured to afford these flask assemblies and liners with enhanced gas exchange with the cultured cells 300 within the flasks over conventional Erlenmeyer flasks used in cell culturing.

It should be emphasized that the above-described embodiments of the present disclosure, including any embodiments, are merely possible examples of implementations, merely set forth for a clear understanding of various principles of the disclosure. For example, the liner 100 and a liner bag 20 with vents 50 can be modified such that its vents 50 have a significantly different shape than the shape depicted in exemplary form in FIG. 3. The vents 50, for instance, can be perforations in the liner bag 20 with the same or similar gas exchange performance as the vents 50 illustrated in FIG. 3. As another example, the flask 120 with cutouts 150 depicted in FIG. 4 can be modified such that its cutouts 150 have a significantly different shape than the shape depicted in exemplary form in FIG. 4. The cutouts 150, for instance, can be arranged in a scaffold- or skeleton-like structure within the sides 126 of the flask 120, thus creating more surface area for enhanced gas exchange with the cell cultures within the liner 100 and liner bag 20 contained within the flask. To accommodate the reduction in the structure of the flask 120, high-strength polymeric materials can be employed for the flask.

According to an aspect (1) of the present disclosure, a liner for an Erlenmeyer flask is provided. The liner comprises: a liner bag comprising a single opening, the bag sized to fit within the flask and having a thickness from about 0.0254 mm to about 0.508 mm, wherein the liner bag is configured for cell culturing and ease of insertion into the flask, and further wherein the liner bag comprises a gas-permeable, polymeric material.

According to an aspect (2) of the present disclosure, the liner of aspect (1) is provided, wherein the liner bag further comprises a pocket adapted to receive a removable flask insertion element.

According to an aspect (3) of the present disclosure, the liner of any of aspects (1)-(2) is provided, wherein the liner bag comprises a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof.

According to an aspect (4) of the present disclosure, the liner of any of aspects (1)-(3) is provided, wherein the liner bag further comprises a vent, the vent having a gas permeability that is greater than the gas permeability of the gas-permeable, polymeric material.

According to an aspect (5) of the present disclosure, the liner of aspect (4) is provided, wherein the vent comprises a membrane with an average pore size from about 0.2 microns to about 5 microns.

According to an aspect (6) of the present disclosure, the liner of aspect (5) is provided, wherein the membrane comprises a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof.

According to an aspect (7) of the present disclosure, the liner of any of aspects (4)-(6) is provided, wherein the liner bag comprises a base and sides, and further wherein the sides comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

According to an aspect (8) of the present disclosure, the liner of any of aspects (1)-(7) is provided, wherein the liner bag further comprises at least one foldable seam configured to facilitate insertion of the bag into the flask.

According to an aspect (9) of the present disclosure, a flask assembly is provided. The flask assembly comprises: an Erlenmeyer flask; and a liner bag comprising a single opening, the bag sized to fit within the flask and having a thickness from about 0.0254 mm to about 0.508 mm, wherein the liner bag is configured for cell culturing and ease of insertion into the flask, and further wherein the liner bag comprises a gas-permeable, polymeric material.

According to an aspect (10) of the present disclosure, the flask assembly of aspect (9)-(10) is provided, wherein the liner bag further comprises a pocket configured to receive a removable flask insertion element.

According to an aspect (11) of the present disclosure, the flask assembly of any of aspects (9)-(10) is provided, wherein the liner bag comprises a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof.

According to an aspect (12) of the present disclosure, the flask assembly of any of aspects (9)-(11) is provided, wherein the liner bag has a thickness of about 0.0254 mm to about 0.254 mm.

According to an aspect (13) of the present disclosure, the flask assembly of any of aspects (9)-(12) is provided, wherein the liner bag further comprises a vent, the vent having a gas permeability that is greater than the gas permeability of the gas-permeable, polymeric material.

According to an aspect (14) of the present disclosure, the flask assembly of aspect (13) is provided, wherein the vent comprises a membrane with an average pore size from about 0.2 microns to about 5 microns.

According to an aspect (15) of the present disclosure, the flask assembly of aspect (14) is provided, wherein the membrane comprises a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof.

According to an aspect (16) of the present disclosure, the flask assembly of any of aspects (13)-(15) is provided, wherein the liner bag comprises a base and sides, and further wherein the sides comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

According to an aspect (17) of the present disclosure, the flask assembly of any of aspects (13)-(16) is provided, wherein the flask comprises a cutout that is sized and positioned to correspond to the vent of the liner bag, as inserted within the flask.

According to an aspect (18) of the present disclosure, the flask assembly of any of aspects (9)-(17) is provided, wherein the liner bag further comprises at least one foldable seam configured to facilitate insertion of the bag into the flask.

According to an aspect (19) of the present disclosure, a flask assembly is provided. The flask assembly comprises: an Erlenmeyer flask comprising a plurality of flask portions; and a liner bag comprising a single opening and sized to fit within the flask, wherein each of the flask portions is configured to couple with at least one of the other flask portions, and further wherein the liner bag is configured for cell culturing and comprises a gas-permeable, polymeric material.

According to an aspect (20) of the present disclosure, the flask assembly of aspect (19) is provided, wherein the liner bag comprises a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof.

According to an aspect (21) of the present disclosure, the flask assembly of any of aspects (19)-(20) is provided, wherein wherein the liner bag has a thickness of about 0.254 mm to about 0.508 mm.

According to an aspect (22) of the present disclosure, the flask assembly of any of aspects (19)-(21) is provided, wherein the liner bag further comprises a vent, the vent having a gas permeability that is greater than the gas permeability of the gas-permeable, polymeric material.

According to an aspect (23) of the present disclosure, the flask assembly of aspect (22) is provided, wherein the vent comprises a membrane with an average pore size from about 0.2 microns to about 5 microns.

According to an aspect (24) of the present disclosure, the flask assembly of aspect (23) is provided, wherein the membrane comprises a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof.

According to an aspect (25) of the present disclosure, the flask assembly of any of aspects (22)-(24) is provided, wherein the liner bag comprises a base and sides, and further wherein the sides comprise a material selected from the group consisting of low density polyethylene (LDPE), polyethylene (PE), ethyl vinyl acetate, silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

According to an aspect (26) of the present disclosure, the flask assembly of any of aspects (22)-(25) is provided, wherein the flask comprises a cutout that is sized and positioned to correspond to the vent of the liner bag, as inserted within the flask.

According to an aspect (27) of the present disclosure, the flask assembly of any of aspects (19)-(26) is provided, wherein each of the flask portions further comprise a registration feature configured to aid in mechanically coupling with the registration feature of at least one of the other flask portions.

Many variations and modifications may be made to the above-described embodiments of the disclosure without departing substantially from the spirit and various principles of the disclosure. All such modifications and variations are intended to be included herein within the scope of this disclosure and protected by the following claims.

What is claimed is:
1. A flask assembly, comprising:
an Erlenmeyer flask; and
a liner bag comprising a single opening and at least one foldable seam, the bag sized to fit within the Erlenmeyer flask and having a thickness from about 0.0254 mm to about 0.508 mm, and the at least one foldable seam being configured to facilitate insertion of the bag into the Erlenmeyer flask,
wherein the liner bag is configured for cell culturing and ease of insertion into the Erlenmeyer flask, and
wherein the liner bag comprises a gas-permeable, polymeric material.
2. The flask assembly according to claim 1, wherein the liner bag further comprises a pocket configured to receive a removable flask insertion element.
3. The flask assembly according to claim 1, wherein the liner bag comprises a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof.

4. The flask assembly according to claim 1, wherein the liner bag has a thickness of about 0.0254 mm to about 0.254 mm.

5. The flask assembly according to claim 1, wherein the liner bag further comprises a vent, the vent having a gas permeability that is greater than the gas permeability of the gas-permeable, polymeric material.

6. The flask assembly according to claim 5, wherein the vent comprises a membrane with an average pore size from about 0.2 microns to about 5 microns.

7. The flask assembly according to claim 6, wherein the membrane comprises a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof.

8. The flask assembly according to claim 5, wherein the liner bag comprises a base and sides, and further wherein the sides comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

9. The flask assembly according to claim 5, wherein the Erlenmeyer flask comprises a cutout that is sized and positioned to correspond to the vent of the liner bag, as inserted within the Erlenmeyer flask.

10. A flask assembly, comprising:
an Erlenmeyer flask; and
a liner bag comprising a single opening and a vent, the bag sized to fit within the Erlenmeyer flask and having a thickness from about 0.0254 mm to about 0.508 mm,
wherein the liner bag is configured for cell culturing and ease of insertion into the Erlenmeyer flask,
wherein the liner bag comprises a gas-permeable, polymeric material, and
wherein the vent comprises a gas permeability that is greater than a gas permeability of the gas-permeable, polymeric material.

11. The flask assembly according to claim 10, wherein the vent comprises a membrane with an average pore size from about 0.2 microns to about 5 microns.

12. The flask assembly according to claim 11, wherein the membrane comprises a material selected from the group consisting of polytetrafluoroethylene (PTFE), perfluoroalkoxy alkane (PFA), high density polyethylene (HDPE) fabric, polyvinylidene fluoride (PVDF) and acrylic copolymer, nylon and combinations thereof.

13. The flask assembly according to claim 10, wherein the liner bag comprises a base and sides, and further wherein the sides comprise a material selected from the group consisting of low density polyethylene (LDPE), polyethylene (PE), ethyl vinyl acetate (EVA), silicone, fluorinated ethylene propylene (FEP), polytetrafluoroethylene (PTFE), perfluoroalkoxy alkane (PFA), polypropylene (PP), polyvinyl chloride (PVC), polyethylene terephthalate (PET), polystyrene (PS), polycarbonate (PC), polymethylpentene (PMP), polyetheretherketone (PEEK), and combinations thereof, and the base comprises a material selected from the group consisting of a polytetrafluoroethylene (PTFE) and a platinum-cured silicone.

14. The flask assembly according to claim 10, wherein the Erlenmeyer flask comprises a cutout that is sized and positioned to correspond to the vent of the liner bag, as inserted within the Erlenmeyer flask.

* * * * *

UNITED STATES PATENT AND TRADEMARK OFFICE
CERTIFICATE OF CORRECTION

| | | |
|---|---|---|
| PATENT NO. | : 11,136,540 B2 | Page 1 of 1 |
| APPLICATION NO. | : 16/095452 | |
| DATED | : October 5, 2021 | |
| INVENTOR(S) | : William Joseph Lacey | |

It is certified that error appears in the above-identified patent and that said Letters Patent is hereby corrected as shown below:

On the Title Page

In Column 2, item [57], Line 2, delete "opening the bag" and insert -- opening, the bag --, therefor.

On page 2, in Column 2, item [56], Line 9, delete "napsus" and insert -- Napus --, therefor.

Signed and Sealed this
Seventh Day of January, 2025

Derrick Brent
*Acting Director of the United States Patent and Trademark Office*